(12) United States Patent
Khanna

(10) Patent No.: US 6,699,269 B2
(45) Date of Patent: Mar. 2, 2004

(54) SELECTIVE BRAIN AND SPINAL CORD HYPOTHERMIA METHOD AND APPARATUS

(75) Inventor: Rohit Kumar Khanna, Daytona Beach, FL (US)

(73) Assignee: Rohit K. Khanna, Daytona Beach, FL (US)

( * ) Notice: Subject to any disclaimer, the term of this patent is extended or adjusted under 35 U.S.C. 154(b) by 2 days.

(21) Appl. No.: 10/136,003

(22) Filed: Apr. 29, 2002

(65) Prior Publication Data

US 2002/0198579 A1 Dec. 26, 2002

Related U.S. Application Data

(60) Provisional application No. 60/287,299, filed on Apr. 30, 2001.

(51) Int. Cl.$^7$ ................................................. A61F 7/00
(52) U.S. Cl. .......................... 607/105; 607/104; 606/23
(58) Field of Search .......................... 607/96, 104–107; 606/20–23, 25–26

(56) References Cited

U.S. PATENT DOCUMENTS

| | | | | |
|---|---|---|---|---|
| 4,904,237 A | * | 2/1990 | Janese | ...................... 604/28 |
| 6,338,727 B1 | * | 1/2002 | Noda et al. | .................. 604/113 |
| 6,379,331 B2 | * | 4/2002 | Barbut et al. | ................. 604/113 |
| 6,506,189 B1 | * | 1/2003 | Rittman et al. | ............... 606/41 |
| 6,527,798 B2 | * | 3/2003 | Ginsburg et al. | ........... 607/106 |

* cited by examiner

Primary Examiner—Roy D. Gibson

(57) ABSTRACT

The invention provides a method and apparatus for performing selective hypothermia to the brain and spinal cord for injury protection without the need for systemic cooling. A flexible catheter is inserted into the cerebral lateral ventricle or spinal subdural space. The catheter has three lumens with a heat transfer element. Two lumens of the catheter circulate a coolant and communicate at the distal heat transfer element for transfer of heat from the cerebrospinal fluid. The third lumen of the catheter allows for drainage of the cerebrospinal fluid. In another embodiment, the catheter has two lumens that circulate the coolant and communicate at the distal heat tranfer element. In another embodiment, a larger surface area cooling template is placed in the subdural space of the brain or the subdural/epidural space of the spine. The template has a conduit that circulates a coolant through the lumen of the template thereby cooling the surrounding brain or spinal cord.

34 Claims, 9 Drawing Sheets

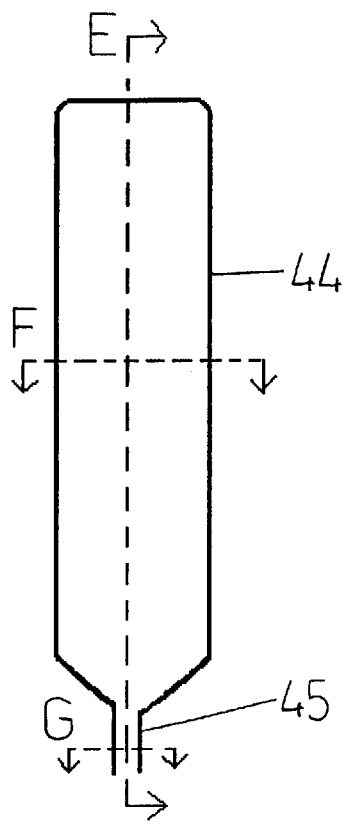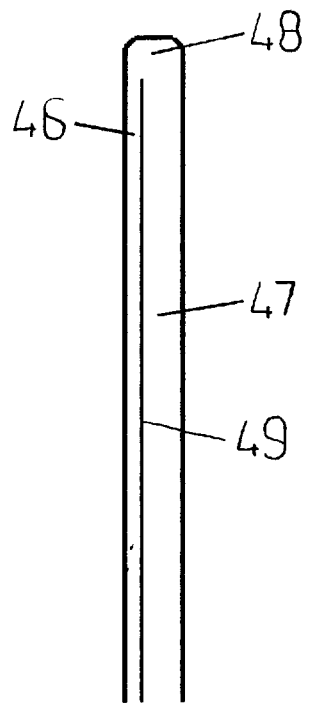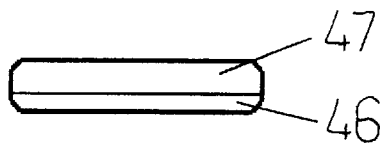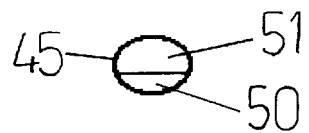
FIG.19　　　　　　FIG.20
FIG.21　　　　　　FIG.22

SELECTIVE BRAIN AND SPINAL CORD HYPOTHERMIA METHOD AND APPARATUS

CROSS REFERENCE TO RELATED APPLICATION

This application claims priority from U.S. Provisional Patent Application No. 60/287,299 filed Apr. 30, 2001, the entire disclosures of which are incorporated herein by reference.

BACKGROUND OF THE INVENTION

The current invention relates to treatment of cerebral swelling as well as regulation of the temperature in the brain and spinal cord. The invention relates to a method and apparatus for altering the temperature of the brain surface and/or the cerebrospinal fluid in the ventricles of the brain and surrounding the spinal cord.

Hypothermia has been shown to provide cerebral and spinal cord injury protection from either trauma, ischemia, or hypoxia. Ischemia may occur from cardiac arrest, cardiac failure, stroke, head or spinal cord injury, aneurysm surgery, cardiac surgery, and aortic or carotid surgery. Hypothermia is also effective in reducing increased intracranial pressure from cerebral swelling. The mechanisms involved in hypothermic cerebral protection are several-fold and include 1) reduction in cerebral glucose and oxygen metabolism and decreasing lactate content following injury, 2) preventing disruption of the blood brain barrier and consequently reducing cerebral edema, 3) reduction of endogenously toxic neurotransmitters like glutamate, glycine, aspartate, acetylcholine, and norepinephrine into the brain after injury, 4) inhibit excessive calcium entry and intracellular calcium overload into neurons, 5) protecting membrane structural proteins like microtubule-associated protein-2, and 6) preventing diffuse axonal injury following brain trauma.

In general, the human brain and spinal cord are maintained at a constant temperature of approximately 37 to 38 degrees celsius. Hypothermia is considered mild when the body temperature is 33 to 35 degrees celsius, moderate between the temperatures of 28 to 32 degrees, and severe in the temperature range of 24 to 28 degrees celsius. Most studies in humans have involved mild to moderate systemic hypothermia mainly because of the significant side effects that occur from induced systemic hypothermia. These include infection, cardiac arrhythmias, coagulopathy, renal failure, as well as rewarming shock. In order to avoid these complications the degree and duration of hypothermia has been shortened thereby limiting its effectiveness.

Generally, cooling of the brain has been accomplished through whole body cooling with use of a cooling blanket, immersing the patient in ice, or cooling the blood through a cardiopulmonary bypass machine. A few methods have been described regarding selective brain and spinal cord hypothermia. These involve cooling the arterial vessel or blood supply to the brain or external cooling helmets, each with its own significant limitations.

Several catheters have been developed to induce systemic hypothermia by inserting them into the bloodstream. More recently catheters have been developed that can be inserted into the arterial vessels to the brain to induce selective brain hypothermia. These catheters are limited in their size and functionality by the small vessel lumen as well the inability to cool all the four major arterial vessels supplying blood to the brain and are unable to cool the spinal cord via this methodology. They also carry the risk of ischemic and thromboembolic stroke by either impairing the blood flow to the brain or dislodging clots that can develop in intra-arterial catheters.

External cooling helmets have limited effectiveness since the blood to the cooled scalp does not circulate into the brain and returns systemically which along with the thick skull dilutes the hypothermic effect to the brain.

Selective brain and spinal cord cooling with insertion of catheters or templates into the ventricular, subdural or epidural space is a novel concept. This avoids the side effects and complications seen from other methods of cooling.

SUMMARY OF THE INVENTION

The invention provides a method and apparatus for performing selective hypothermia to the brain and/or the spinal cord for injury protection without the need for systemic cooling.

For selective brain cooling, in one embodiment of the present invention, a flexible catheter is inserted into the cerebral lateral ventricle to cool the cerebrospinal fluid and henceforth the brain. The catheter has three lumens with a distal heat conductive element which also has holes to allow for drainage of cerebrospinal fluid. The inner-most lumen is connected with the outer-most lumen at the tip of the catheter and allows for circulation of a coolant. The intermediate lumen has holes at the distal end that allows for drainage of cerebrospinal fluid as well as intracranial pressure monitoring similar to a ventriculostomy. An occipital approach to the placement of the catheter is preferred to allow for a longer catheter with more surface area for heat exchange. In another embodiment of this catheter, the inner-most lumen allows for drainage and the intermediate lumen is connected with the outer lumen for circulation of the coolant.

For selective spinal cord cooling, in another embodiment of the catheter described above, a catheter with a longer distal heat conductive element is inserted into the lumbar subdural or epidural space to allow for cooling around the spinal cord. This catheter may or may not have a lumen for drainage of cerebrospinal fluid.

In another embodiment for selective brain cooling, a larger surface area template is inserted into the subdural space either through a burr-hole or following a craniotomy. These templates have variable sizes with small thickness and circulate a coolant with a wider surface area to allow placement in the subdural space to directly cool the brain surface. These templates can also be placed in the epidural space of the spine for selective spinal cord cooling.

The catheters and templates are designed to allow an inert coolant to circulate in the lumens without direct exposure to the brain or spinal cord and thereby altering the brain or spinal cord temperature. This allows for selective cooling of the brain and spinal cord for treatment of injury from trauma, ischemia, hypoxia and/or cerebral swelling. The length and size of the catheters and templates is variable to allow for a wide selection and patient individuality.

BRIEF DESCRIPTION OF THE DRAWINGS

A better understanding of the present invention will be had after a reading of the following detailed description taken in conjunction with the accompanying drawings wherein:

FIG. 19 is a cross-sectional top view of another embodiment of the template

FIG. 20 is a cross-sectional side view of the template taken along line E in FIG. 19

FIG. 21 is a cross-sectional view of the template taken along line F in FIG. 19

FIG. 22 is a cross-sectional view of the template conduit taken along line G in FIG. 19

DETAILED DESCRIPTION OF THE PREFERRED EMBODIMENTS

Figure 1:
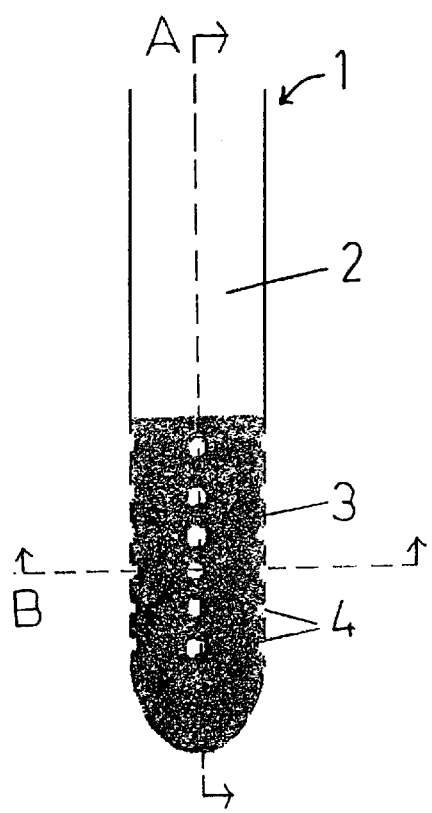
FIG. 1 is a top view of one embodiment of the catheter

In one method of selective brain and/or spinal cooling, a catheter as shown in FIG. 1, can be placed into the ventricle of the brain or the subdural space of the spine. This allows for cooling of the cerebrospinal fluid and hence the brain and/or spinal cord selectively. The catheter 1 has a proximal portion 2 and a distal heat transfer element 3. The distal heat transfer element 3 has several circumferential holes 4 that allow drainage of cerebrospinal fluid.

Figure 2:
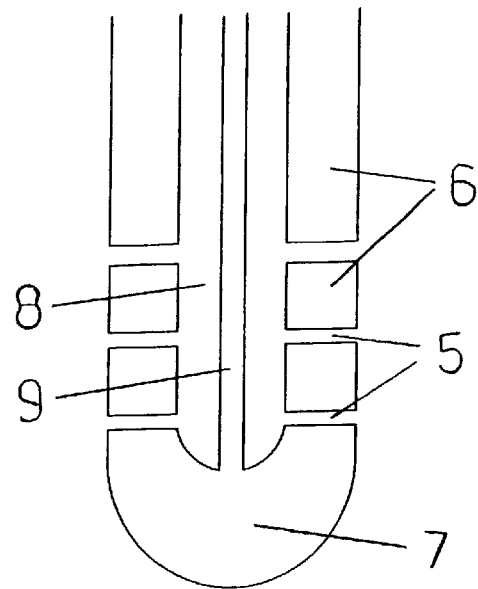
FIG. 2 is a cross-sectional side view of the catheter taken along line A in FIG. 1
Figure 3:
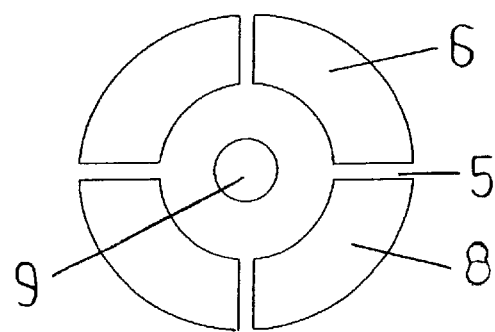
FIG. 3 is a cross-sectional view of the catheter taken along line B in FIG. 1

In one embodiment of the cooling catheter as shown in FIGS. 2 & 3, the heat exchange fluid or compressed refrigerant enters through the central lumen 9 into the distal end of the heat transfer element 7. The coolant or the gaseous refrigerant returns through the outer lumen 6. The circulation of the coolant through the catheter cools the distal heat transfer element, thereby allowing the cerebrospinal fluid surrounding the catheter to be cooled. The middle lumen 8 provides for drainage of the cerebrospinal fluid through the holes 5.

Figure 4:
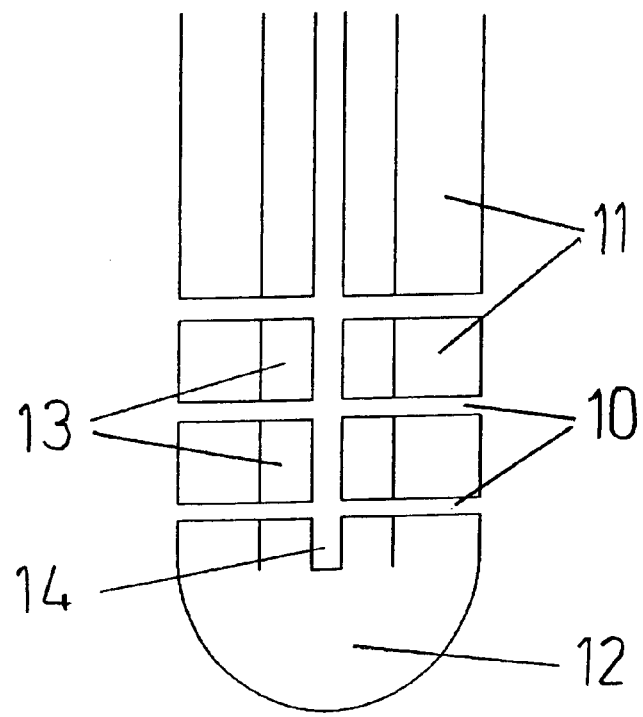
FIG. 4 is a cross-sectional side view of another embodiment of the catheter
Figure 5:
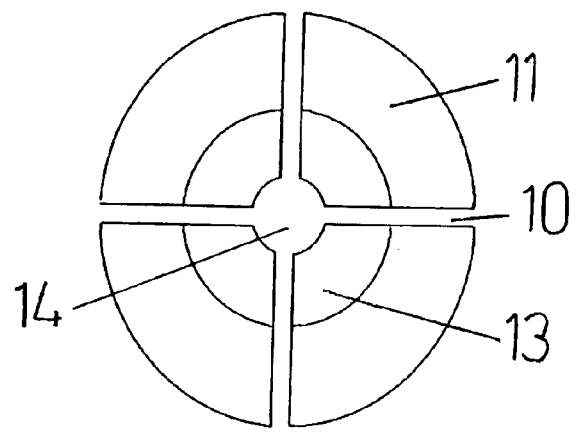
FIG. 5 is a cross-sectional view of the catheter in FIG. 4

In another embodiment of the cooling catheter as shown in FIGS. 4 & 5, a coolant enters through the middle lumen 13 into the distal end of the heat transfer element 12 and returns through the outer lumen 11. The central lumen 14 allows drainage of the cerebrospinal fluid through the holes 10.

Figure 6:
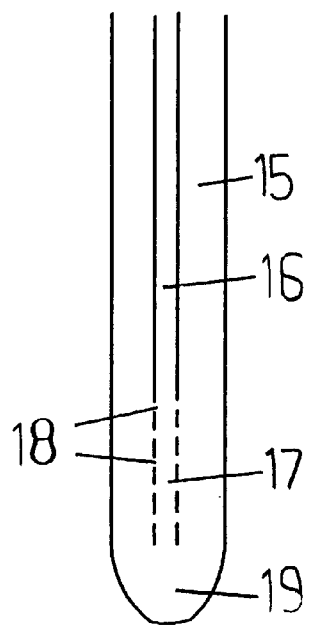
FIG. 6 is a cross-sectional side view of another embodiment of the catheter
Figure 7:
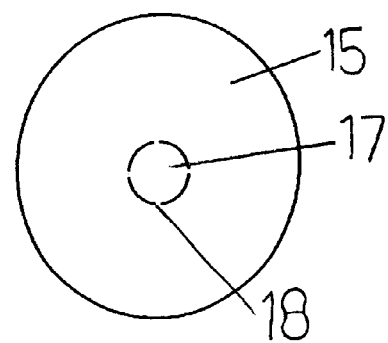
FIG. 7 is a cross-sectional view of the catheter in FIG. 6
Figure 8:
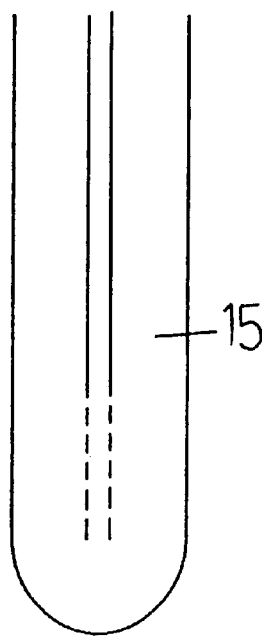
FIG. 8 is a cross-sectional side view of another embodiment of the catheter

In another embodiment of the cooling catheter, as shown in FIGS. 6 & 7, a coolant enters through the central lumen 16 into the elongated distal heat transfer element 19. The central lumen has holes in the sides 18 that create some turbulence in the heat transfer element 19, thereby facilitating the transfer of heat. The coolant returns through the outer lumen 15. In a modification of this embodiment as shown in FIG. 8, the outer lumen 15 can expand with increased pressure from the circulating coolant, thereby increasing the outer surface area of the heat transfer element to allow rapid heat exchange.

Figure 9:
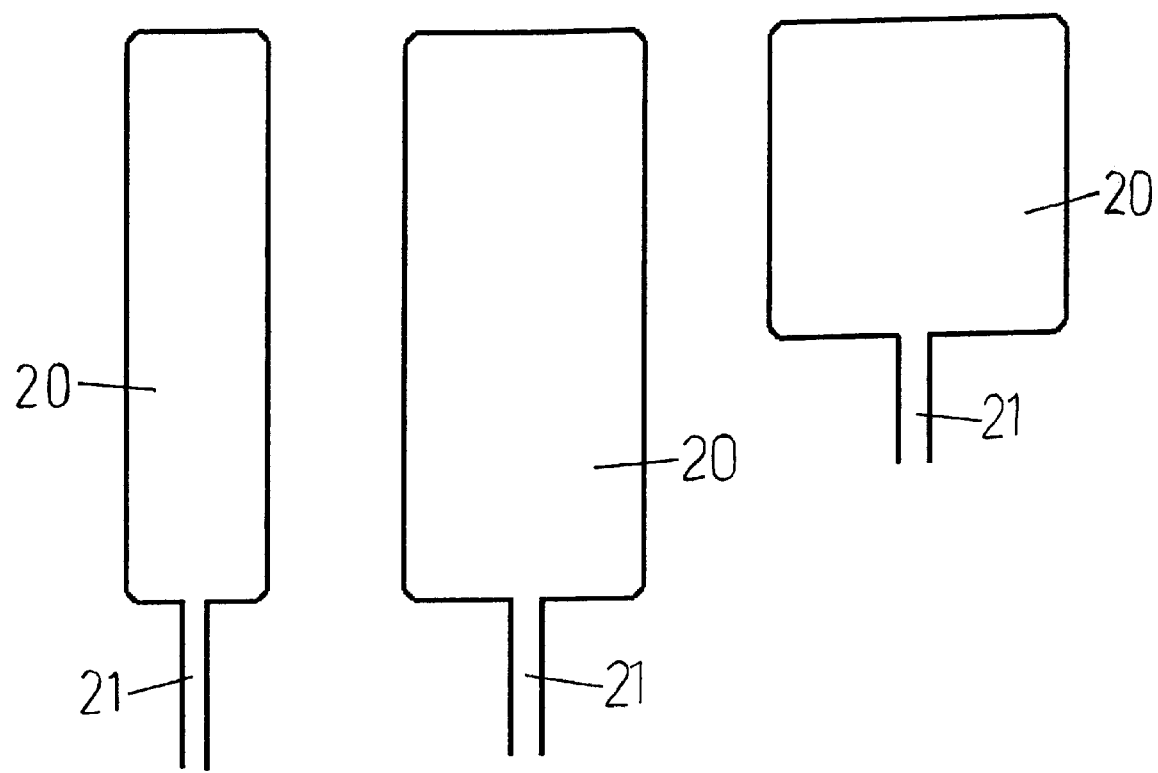
FIG. 9 is a top view of various sized templates

For more selected cooling of the brain or spinal cord, a template of varying sizes can be used overlying the area of the central nervous system in need of hypothermia. FIG. 9 is an illustration of some of the various sizes of the templates. The length and width may vary but the thickness is uniform to allow for a low profile in the subdural or epidural space of the brain or spine. The cooling templates consist of a proximal conduit 21 and a template 20.

Figure 10:
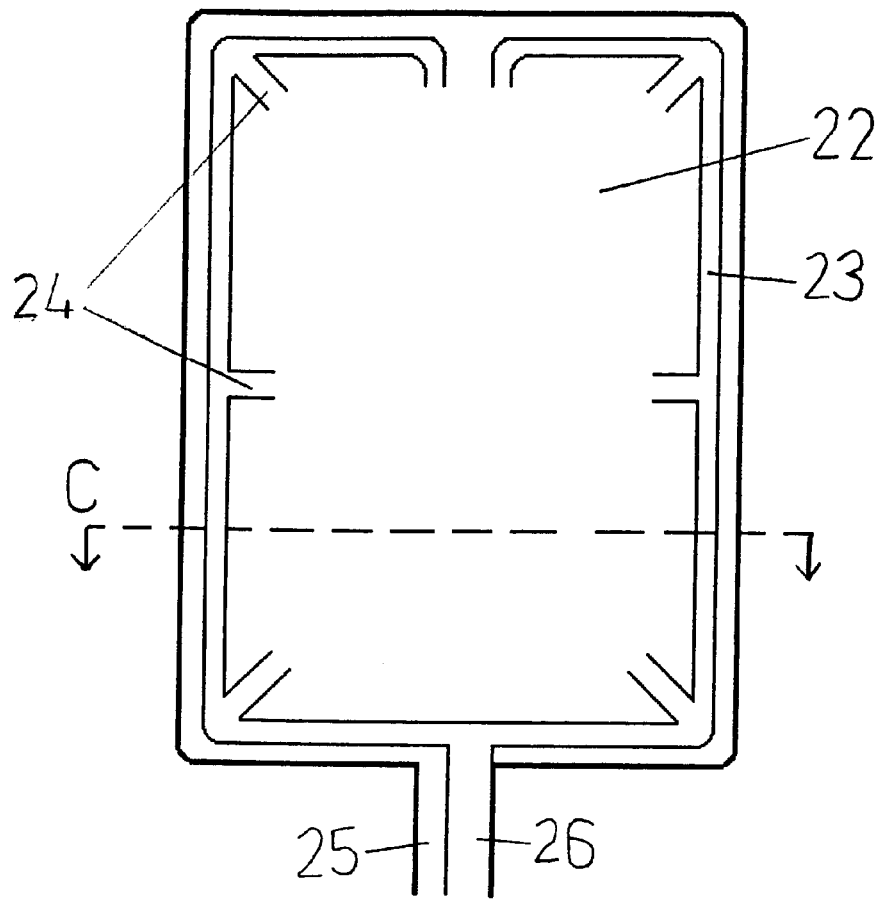
FIG. 10 is a cross-sectional top view of a template
Figure 11:
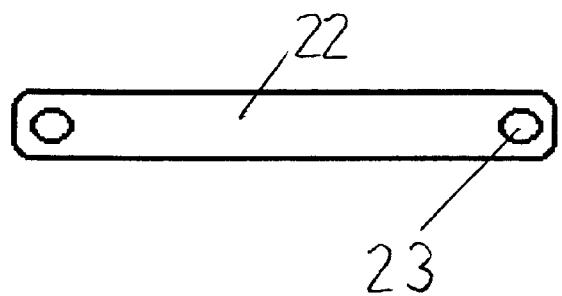
FIG. 11 is a cross-sectional view of the template taken along line C in FIG. 10

In one embodiment of the cooling template as shown in FIGS. 10 & 11, the proximal conduit has two lumens 25 & 26. One of the conduit lumens 26 supplies the cooled heat exchange fluid or compressed refrigerant to the template lumen 22. The template has internal conduits 23 & 24 which introduce the coolant into the lumen 22 through which the heat exchange fluid circulates and is returned through the other conduit lumen 25 for external cooling.

Figure 12:
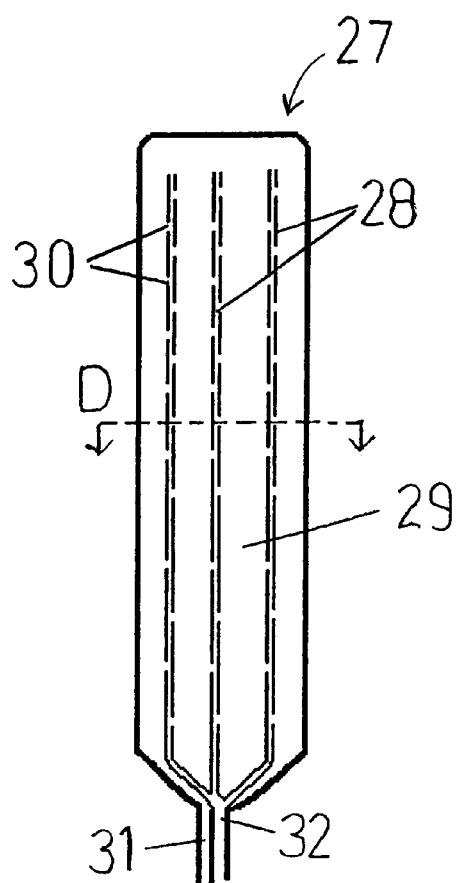
FIG. 12 is a cross-sectional top view of another embodiment of the template
Figure 13:
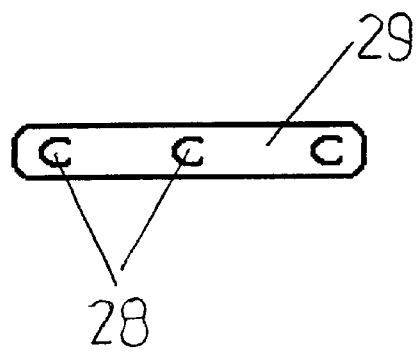
FIG. 13 is a cross-sectional view of the template taken along line D in FIG. 12
Figure 14:
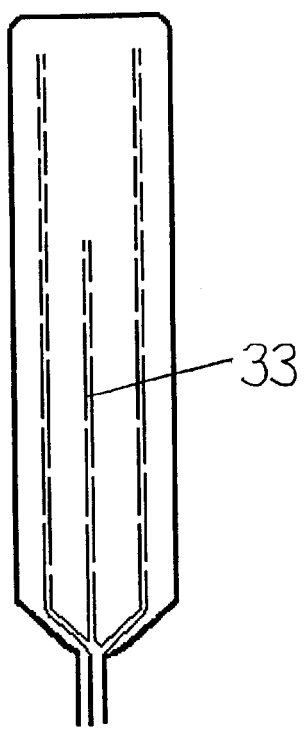
FIG. 14 is a cross-sectional top view of another embodiment of the template
Figure 15:
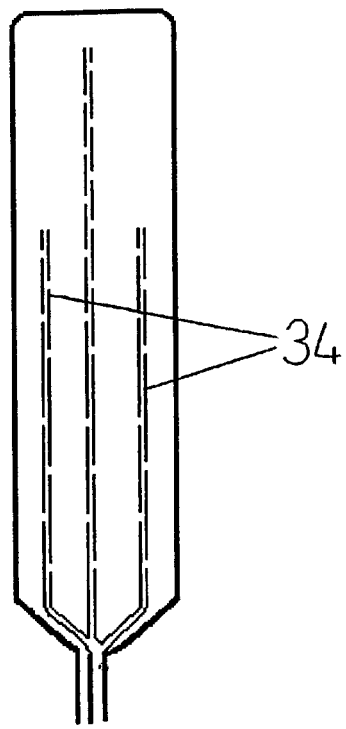
FIG. 15 is a cross-sectional top view of another embodiment of the template

In another embodiment of the cooling template as shown in FIGS. 12 & 13, the proximal conduit has two lumens 31 & 32. One of the conduit lumens 32 supplies the cooled heat exchange fluid or compressed refrigerant to the template lumen 29. The template has internal conduits 28 with holes on the sides 30 which introduce the coolant into the lumen 29 through which the coolant circulates and is returned through the conduit lumen 31 for external cooling. FIG. 14 illustrates another embodiment of the template with a shorter central internal conduit 33. FIG. 15 illustrates yet another embodiment of the template with shorter outermost internal conduits 34.

Figure 16:
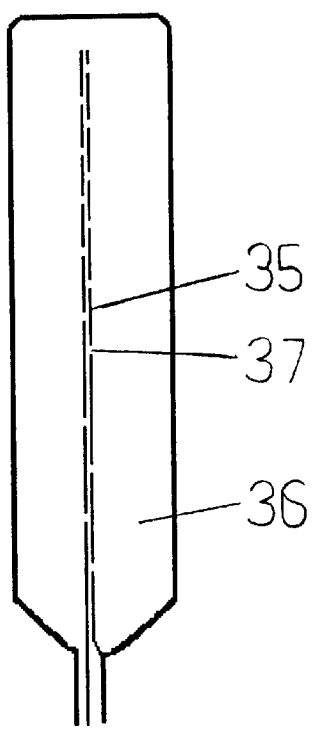
FIG. 16 is a cross-sectional top view of another embodiment of the template

In another embodiment of the cooling template as illustrated in FIG. 16, there is a single internal conduit 35 in the template lumen 36 with side holes 37.

Figure 17:
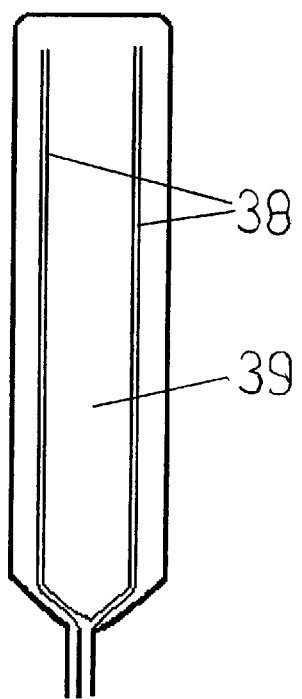
FIG. 17 is a cross-sectional top view of another embodiment of the template
Figure 18:
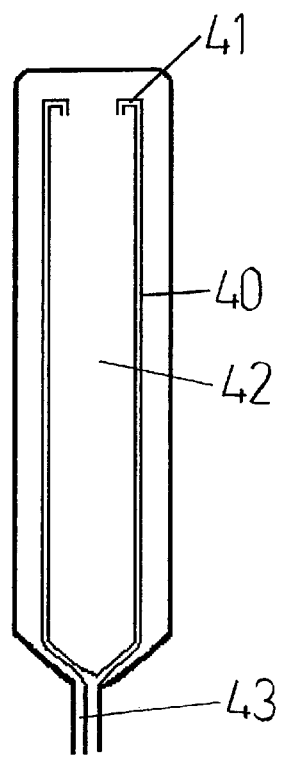
FIG. 18 is a cross-sectional top view of another embodiment of the template

FIG. 17 illustrates another embodiment of the cooling template with two internal conduits without side holes 38 in the template lumen 39. In another embodiment illustrated in FIG. 18, the internal conduits 40 have a curved tip at the distal ends 41. This allows the coolant to flow in the template lumen 42 from the distal end to the proximal end where it is returned to an external cooler through the conduit lumen 43.

In yet another embodiment of the cooling template as shown in FIGS. 19 to 22, the proximal conduit 45 has a lumen 50 through which the coolant enters the template 44. The template has two lumens 46 & 47 separated by a membrane 49. The two template lumens 46 & 47 communicate at the distal end 48. The coolant enters the template lumen 46 and is returned through template lumen 47 and conduit lumen 51 to an external cooler.

While the present invention has been described in conjunction with preferred embodiments and methods, it is intended that the description and accompanying drawings shall be interpreted as only illustrative of the invention. It is evident that those skilled in the art may make numerous uses and modifications of and departures from the specific embodiments described herein without departing from the inventive concept.

REFERENCES
U.S. Patent Documents

| | | |
|---|---|---|
| 3425419 | February 1969 | Dato. |
| 4111209 | September 1978 | Wolvek. |
| 4745922 | May 1988 | Taylor. |
| 4850958 | July 1989 | Berry et al. |
| 4941475 | July 1990 | Williams et al. |
| 4987896 | January 1991 | Nakamatsu. |
| 5098376 | March 1992 | Berry et al. |
| 5151100 | September 1992 | Abele et al. |
| 5188602 | February 1993 | Nichols. |
| 5257977 | November 1993 | Eshel. |
| 5261399 | November 1993 | Klatz et al. |
| 5269749 | December 1993 | Koturov. |
| 5269758 | December 1993 | Taheri. |
| 5281213 | January 1994 | Milder et al. |
| 5334193 | August 1994 | Nardella. |
| 5344436 | September 1994 | Fontenot et al. |
| 5365750 | November 1994 | Greenthal. |
| 5403281 | April 1995 | O'Neill. |
| 5417686 | May 1995 | Peterson. |
| 5437673 | August 1995 | Baust et al. |
| 5462521 | October 1995 | Brucker et al. |
| 5647051 | July 1997 | Neer. |
| 5833671 | November 1998 | Macoviak et al. |
| 5624392 | April 1997 | Saab. |
| 5716386 | February 1998 | Ward et al. |
| 5837003 | November 1998 | Ginsburg. |
| 5902268 | May 1999 | Saab |
| 5904670 | May 1999 | Schreiner. |
| 5913885 | June 1999 | Klatz et al. |
| 5957963 | September 1999 | Dobak, III. |
| 6019783 | February 2000 | Philips. |
| 6033383 | March 2000 | Ginsburg. |
| 6042559 | March 2000 | Dobak, III. |
| 6051019 | April 2000 | Dobak, III. |
| 6110168 | August 2000 | Ginsburg. |
| 6126684 | October 2000 | Gobin et al. |
| 6251130 | June 2001 | Dobak, III, et al. |
| 6264679 | July 2001 | Keller et al. |
| 6287326 | September 2001 | Pecor. |
| 6312452 | November 2001 | Dobak, III, et al. |
| 6325818 | December 2001 | Werneth. |
| 6338727 | January 2002 | Noda et al. |

What is claimed is:

1. A method for selectively cooling the central nervous system comprising the steps of: A. providing a heat exchange catheter device which comprises; i) an elongate flexible catheter with a proximal and distal end, ii) two lumens which communicate at the distal end through which a heat exchange fluid is circulated, iii) a heat exchanger located at the distal end of the catheter allowing transfer of heat between the said heat exchanger and its surroundings; B. inserting the catheter into a cerebrospinal fluid or epidural space; C. circulating the heat exchange fluid with temperature below the body temperature through the catheter, thereby transferring heat from the cerebrospinal fluid to the cool heat exchange fluid and subsequently cooling the central nervous system.

2. The method of claim 1, further comprising the steps of: D. providing a temperature sensor placed on the said catheter at or adjacent to the distal end of the catheter so that it senses the temperature of the cerebrospinal fluid and/or the central nervous system; E. providing an external heat exchange fluid temperature and flow regulator connected to the proximal end of the said catheter; F. achieving a desired temperature of the central nervous system by controlling the amount of heat transferred between the heat exchanger and the cerebrospinal fluid through regulation of the heat exchange fluid temperature and flow rate.

3. The method of claim 1, wherein the said catheter further comprises one or more sensors at or adjacent to the distal end of the catheter selected from a group consisting of: pressure, temperature, oxygenation, carbonation, metabolite, and pH sensors.

4. The method of claim 1, wherein the said heat exchanger is made from a material selected from die group comprising of: metal, plastic, or latex.

5. The method of claim 1, wherein the said heat exchange fluid is made from a material selected from the group comprising of: a compressed refrigerant, a coolant, saline, lactated Ringer's solution, or water cooled by extracorporeal refrigeration.

6. The method of claim 1, wherein a coolant in the liquid form circulates to the said distal heat exchanger which acts like an evaporator thereby transferring heat from the surrounding area and returning the coolant in its gaseous format to an external condenser.

7. The method of claim 1, wherein the said cerebrospinal fluid space being a ventricle of the brain with the said catheter secured to the skull.

8. A method of claim 1, wherein hypothermia is used for cerebral insult following either trauma, ischemia, hypoxia, seizure, and/or cerebral swelling.

9. The method of claim 1, wherein the said cerebrospinal fluid space being the subarachnoid or subdural space of die spine thereby selectively cooling the spinal cord.

10. The method of claim 1, wherein the said catheter is placed in the epidural space of the spine.

11. A method of claim 1, wherein hypothermia is used for protection of the spinal cord following either trauma, ischemia, swelling, or aortic aneurysm surgery.

12. The method of claim 1, wherein the said catheter outer lumen expands when the heat exchange fluid is circulated.

13. The method of claim 1, wherein the said catheter is placed in the epidural space of the spine.

14. A method for selectively cooling the central nervous system comprising the steps of: A. providing a flexible elongated catheter with three lumens and a distal heat conductive element with one of the lumens communicating with the external space through one or more ports at the distal end; B. inserting the catheter into the cerebrospinal fluid space of the brain or the subdural space of the spine; C. circulating a cool fluid through one of the catheter lumens which communicates with a second lumen at the distal heat conductive element of the catheter thereby cooling the cerebrospinal fluid without any exposure of the circulating fluid to the external environment; D. the third lumen of the catheter providing cerebrospinal fluid drainage through said ports communicating from the lumen to the external environment at the distal end of the catheter.

15. The method of claim 14, further comprising the steps of: F. providing a temperature sensor placed on the said catheters at or adjacent to the distal end of the catheter so that it senses the temperature of the cerebrospinal fluid; G. providing an external circulating fluid temperature and flow regulator connected to the proximal end of the said first catheter; H. achieving a desired temperature of the cerebrospinal fluid through regulation of the circulating fluid temperature and flow rate; I. providing a pressure sensor placed on the said catheters at or adjacent to the distal end of the catheter so that it senses the pressure of the cerebrospinal fluid and/or brain; I. maintaining the cerebrospinal fluid and/or brain pressure within a desired range through regulation of the circulating fluid flow rate and amount of cerebrospinal fluid drainage.

16. The method of claim 14, wherein the said catheter further comprises one or more sensors at or adjacent to the distal end of the catheter selected from a group consisting of:

pressure, temperature, oxygenation, carbonation, metabolite, and pH sensors.

17. The method of claim 14, wherein the said conductive element is made from a material selected from the group consisting of: metal, plastic or latex.

18. The method of claim 14, wherein the said cool fluid is made from a material selected from the group consisting of: a compressed refrigerant, a coolant, saline, lactated Ringer's solution, or water cooled by extracorporeal refrigeration.

19. The method of claim 14, wherein a coolant in the liquid form circulates to the said distal heat conductive element which acts like an evaporator thereby transferring heat from the surrounding area and returning the coolant in its gaseous format to an external condenser.

20. The method of claim 14, wherein said cerebrospinal fluid space being a ventricle of the brain with the said catheter secured to the skull.

21. The method of claim 14, wherein hypothermia is used for cerebral insult following either trauma, ischemia, hypoxia, seizure, and/or cerebral swelling.

22. The method of claim 14, wherein the said cerebrospinal fluid space being the subdural space of the spine thereby selectively cooling the spinal cord.

23. The method of claim 14, wherein hypothermia is used for protection of the spinal cord following either trauma, ischemia, swelling, or aortic aneurysm surgery.

24. The said catheter of claim 14, wherein the outer lumen expands when the heat exchange fluid is circulated.

25. A method for selectively cooling the central nervous system comprising the steps of: A. providing a flexible heat exchange template of varying length and width with small thickness and a proximal and distal end; B. proximal end of the said heat exchange template consisting of a conduit that allows heat exchange fluid to circulate in the template lumen; C. inserting the template into the subdural or epidural space of the brain or spinal cord; D. circulating the heat exchange fluid with temperature below the body temperature through the template, thereby transferring heat from the nervous system to the cool heat exchange fluid; E. returning the heat exchange fluid through the proximal conduit to an external cooler.

26. The method of claim 25, wherein insertion of the template into the subdural or epidural space of the brain follows a craniotomy or burr hole placement.

27. The method of claim 25, wherein insertion of the template into the subdural or epidural space of the spinal cord follows a laminectomy or laminotomy.

28. The method of claim 25, further comprising the steps of: F. providing a temperature sensor placed on the said template so that it senses the temperature of the brain or spinal cord; G. providing an external heat exchange fluid temperature and flow regulator connected to the proximal end of the said template; H. achieving a desired temperature of the brain or spinal cord by controlling the amount of heat transferred from the heat exchanger through regulation of the heat exchange fluid temperature and flow rate.

29. The method of claim 25, wherein the said template further comprises one or more sensors at or adjacent to the distal end of the catheter selected from a group consisting of: pressure, temperature, oxygenation, carbonation, metabolite, and pH sensors.

30. The method of claim 25, wherein the said heat exchange fluid circulates through two lumens in the said template which communicate at the distal end.

31. The method of claim 25, wherein the said heat exchange fluid enters the said template through one or more internal conduits of various lengths in the said lumen of the template.

32. The method of claim 25, wherein the said heat exchange template is made from a material selected from the group comprising of: metal, plastic, or latex.

33. The method of claim 25, wherein the said heat exchange fluid is made from a material selected from the group comprising of: a compressed refrigerant, a coolant, saline, lactated Ringer's solution, or water.

34. The method of claim 25, wherein the said template includes a working lumen with a distal port for communicating with the subarachnoid, subdural or epidural space.

* * * * *